United States Patent
Vogel et al.

(10) Patent No.: US 6,462,098 B1
(45) Date of Patent: Oct. 8, 2002

(54) PROCESS FOR PRODUCING LIQUID AND, OPTIONALLY, GASEOUS PRODUCTS FROM GASEOUS REACTANTS

(75) Inventors: Alex Philip Vogel, Parys (ZA); Andre Peter Steynberg, Vanderbijlpark (ZA); Peter Jacobus Van Berge, Sasolburg (ZA)

(73) Assignee: Sasol Technology (Proprietary) Limited, Johannesburg (ZA)

( * ) Notice: Subject to any disclaimer, the term of this patent is extended or adjusted under 35 U.S.C. 154(b) by 0 days.

(21) Appl. No.: 09/916,657

(22) Filed: Jul. 25, 2001

Related U.S. Application Data

(63) Continuation of application No. PCT/IB00/00093, filed on Feb. 1, 2000.

(30) Foreign Application Priority Data

Feb. 5, 1999 (ZA) .................................................. 99/0936

(51) Int. Cl.$^7$ ........................ C07C 27/00; B01D 29/85; B01D 29/07
(52) U.S. Cl. ........................ 518/700; 518/728; 210/497; 210/497.1
(58) Field of Search ................................ 518/700, 728; 210/497.01, 497.1

(56) References Cited

U.S. PATENT DOCUMENTS

| | | | |
|---|---|---|---|
| 5,382,748 A | 1/1995 | Behrmann et al. | 585/899 |
| 5,527,473 A | 6/1996 | Ackerman | 210/767 |
| 5,599,849 A * | 2/1997 | Jager et al. | |
| 5,811,469 A | 9/1998 | Leviness et al. | 518/700 |

FOREIGN PATENT DOCUMENTS

| | | |
|---|---|---|
| EP | 0609079 | 8/1994 |
| GB | 589779 | 6/1947 |
| WO | 9903574 * | 1/1999 |

* cited by examiner

Primary Examiner—Jafar Parsa
(74) Attorney, Agent, or Firm—Ladas & Parry

(57) ABSTRACT

A process for producing liquid and, optionally, gaseous products from gaseous reactants feeds (18), at a low level, gaseous reactants into a slurry bed of solid catalyst particles (14) suspended in a suspension liquid. The gaseous reactants are allowed to react as they pass upwardly through the slurry bed (14), hereby to form liquid and, optionally, gaseous products. The reaction is catalyzed by the catalyst particles. Liquid product is separated from the catalyst particles by passing, in a filtration zone (22) within the slurry bed, liquid product through a filtering medium having a plurality of openings through which the liquid passes. The openings have a controlling dimension of x microns. The proportion of catalyst particles, which have a particle size smaller than x microns, in the slurry bed is less than 18% by volume based on the total volume of the catalyst in the slurry bed.

8 Claims, 6 Drawing Sheets

PROCESS FOR PRODUCING LIQUID AND, OPTIONALLY, GASEOUS PRODUCTS FROM GASEOUS REACTANTS

This application is a continuation of copending application International Application PCT/IB00/00093 filed on Feb. 1, 2000 and which designated the U.S., and was published in English, claims the benefit thereof and incorporates the same by reference.

FIELD OF INVENTION

This invention relates to a process for producing liquid and, optionally, gaseous products from gaseous reactants.

SUMMARY OF INVENTION

According to a first aspect of the invention, there is provided a process for producing liquid and, optionally, gaseous products from gaseous reactants, which process comprises feeding, at a low level, gaseous reactants into a slurry bed of solid catalyst particles suspended in a suspension liquid;

allowing the gaseous reactants to react as they pass upwardly through the slurry bed, thereby to form liquid and, optionally, gaseous products, with the reaction being catalyzed by the catalyst particles; and separating liquid product from the catalyst particles by passing, in a filtration zone within the slurry bed, liquid product through a filtering medium having a plurality of openings through which the liquid passes, with the openings having a controlling dimension of x microns, and with the proportion of catalyst particles, which have a particle size smaller than x microns, in the slurry bed being less than 18% by volume based on the total volume of the catalyst in the slurry bed.

A low proportion, or even absence, of such fine catalyst particles in the slurry bed ensures a high solids separation efficiency across the filtering medium, and also ensures a low degree of catalyst contamination of the liquid product downstream of the filtering medium; however, as also described in more detail hereunder, it has surprisingly been found that high conversions of gaseous reactants to products are nevertheless obtainable in the process. Thus, a low proportion of less than 4 vol %, preferably less than 2 vol %, catalyst particles smaller than x microns, normally ensures that the liquid product has a catalyst content less than 10 ppm (by mass)

By 'controlling dimension' in respect of the filtering medium openings or filtering openings is meant the maximum dimension of the filtering openings through which the catalyst particles can pass. The controlling dimension may, for example, be obtained from the filter manufacturer's specification. Thus, it may be the upper tolerance level, or it may be the average gap size added to a factor of, e.g. three times, the gap size standard deviation.

The filtering openings may thus be of any desired shape. In one embodiment, the filtering medium openings, when seen in the direction of liquid flow through the openings, may be circular, with the controlling dimension of each opening thus being its diameter. Instead, in another embodiment, the filtering medium openings, when seen in the direction of liquid flow through the openings, may be more-or-less rectangular so that the width of each opening is shorter than its length, with the controlling dimension of each opening being its width.

Thus, for example, x may typically be 40 microns. The filtering medium may then, for example, be a wedge wire filtering medium comprising parallel wires which are spaced so as to provide openings whose average widths are 10 microns, i.e. the filtering medium has a nominal opening or gap size of 10 microns; the opening widths thus vary or deviate from 10 microns, with the average width being 10 microns, while the maximum width or gap size is 40 microns. The slurry bed will then contain less than 18% by volume (based on the volume of the total catalyst inventory of the bed) of catalyst particles having a diameter less than 40 microns, ie particles smaller than 40 microns.

The proportion of catalyst particles smaller than x microns in the slurry bed may thus be less than 18% by volume at the start of a catalyst run, ie when the catalyst is initially loaded in a slurry phase reactor or on initial formation of the slurry bed at the start of the ruin. However, during the course of the run, the proportion of catalyst particles smaller than x microns is worked down, through normal operation of the slurry bed, to less than 4 vol %, and preferably less than 2 vol %. Accordingly, the slurry bed may typically contain substantially no catalyst particles smaller than x microns for at least a major portion of the catalyst run, eg for substantially the entire run.

In a particular embodiment of the invention, the controlling dimension of the filtering medium openings may be their minimum dimension, with the proportion of catalyst particles, whose minimum dimension is less than x microns, in the slurry bed being less than 4% by volume based on the total volume of the catalyst in the slurry bed.

While the process can, at least in principle, have broader application, it is envisaged that the suspension liquid will normally, but thus not necessarily always, be the liquid product.

Furthermore, while it is also believed that, in principle, the process can have broader application, it is envisaged that it will have particular application in hydrocarbon synthesis where the gaseous reactants are capable of reacting catalytically in the slurry bed to form liquid hydrocarbon product and, optionally, gaseous hydrocarbon product. In particular, the hydrocarbon synthesis may be Fischer-Tropsch synthesis, with the gaseous reactants being in the form of a synthesis gas stream comprising mainly carbon monoxide and hydrogen, with both liquid and gaseous hydrocarbon products being produced, and with the catalyst particles thus being Fischer-Tropsch catalyst particles.

The slurry bed will thus be provided in a suitable vessel, eg a column, with unreacted reactants and gaseous product being withdrawn from the vessel above the slurry bed, and the separated liquid product also being withdrawn from the vessel. The vessel will be maintained at normal elevated pressure and temperature conditions associated with Fischer-Tropsch synthesis, eg a predetermined operating pressure in the range 10 to 50 bar, and at a predetermined temperature in the range 180° C. and 280° C., or even higher for the production of lower boiling point product.

Any suitable filtering medium can, at least in principle, be used, and the filtering medium may have differing opening or gap sizes. However, all the openings of the filtering medium will normally be of nominally the same size and have the same geometry. The filtering medium may be part of a filter cartridge or element mounted in the vessel, and may be of a type which is of elongate form, with the filtering medium being of cylindrical form and enclosing a filtrate collecting zone, and with a filtrate outlet for withdrawing filtrate, ie liquid product, being provided at one end thereof. While, in principle, the filtering medium can be any desired filtering medium having the desired opening size to prevent catalyst particles passing therethrough, it is preferably of a type or construction with which permanent clogging or impregnation thereof with the catalyst particles does not readily occur. Thus, the filtering medium can be a mesh, eg a woven mesh; a porous material such as a ceramic material; a perforated sheet; spiral wire wound, eg from wedge wire; or the like.

The maximum allowable controlling dimension of the filtering medium will thus be dictated by the portion of catalyst particle sizes smaller than the controlling dimension of the filter, present in the slurry bed. Although, in slurry phase reactions, catalyst breakup due to attrition normally takes place, resulting in a lowering of the minimum particle size, and a decrease in the average catalyst particle size, it has surprisingly been found that catalyst breakup by attrition or any other means of disintegration can be almost entirely avoided.

The catalyst particles can, at least in principle, be any desired supported Fischer-Tropsch catalyst, such as an iron-based catalyst, a cobalt-based catalyst, or any other Fischer-Tropsch catalyst. Supported catalysts, which are physically stronger than unsupported catalysts, are typically used, and supported cobalt catalysts are preferred. Preferably, the catalyst may be that obtained by a preparation method as described in ZA 96/2759//U.S Pat. No. 5,733,839 or ZA 99/1265//PCT/GB99/00527. Such a method is hereinafter also referred to as 'the proprietary method', and the catalyst obtained is hereinafter also referred to as the 'proprietary cobalt Fischer-Tropsch catalyst'. ZA 96/2759//U.S. Pat. No. 5,733,839 and ZA 99/1265//PCT/GB99/00527, are hence incorporated herein by reference thereto. It was surprisingly found that catalysts produced in this manner are sufficiently strong so that little or no attrition thereof during extended runs at normal slurry bed operating conditions occurs. In other words, it was surprisingly found that, when the catalyst which is used in the process is prepared in accordance with the method of ZA 96/2759//U.S. Pat. No. 5,733,839 or ZA 99/1265//PCT/GB99/00527, the catalyst particle size distribution can be selected so that there are less than 5 vol % of particles smaller than 45 microns initially present; moreover, it was surprisingly found with these catalysts that the particle size distribution remains more-or-less unchanged during operation under normal operating conditions, ie there normally is little or no attrition into particles smaller than 45 microns.

When using catalyst particles that are physically strong, eg supported cobalt catalyst particles, it is important to ensure that the slurry bed at all times does not contain an appreciable proportion of catalyst particles of a size close to the aperture or opening size of the filtering medium, ie near gap-size particles, since such sized particles can cause permanent blockage of the filtering medium.

The process of the invention thus permits the selection of an optimized catalyst size distribution for a Fischer Tropsch catalyst based on a specific catalyst support, with the catalyst having sufficient strength and an appropriate size distribution to maximize synthesis performance and to ensure trouble free extended continuous operation of the reactor vessel. The production of sufficiently strong catalysts is, as set out hereinbefore, described in ZA 96/2759//U.S. Pat. No. 5,733,839 and ZA 99/1265//PCT/GB99/00527, and comprises mixing a modified catalyst support with an aqueous solution of an active catalyst component or its precursor, to form a slurry, and impregnating the protected modified catalyst support with the active catalyst component or its precursor, to form the catalyst. The method of modifying the catalyst support comprises introducing onto and/or into an untreated catalyst support which is partially soluble in an aqueous acid solution and/or a neutral aqueous solution, a modifying component capable, when present in or on the catalyst support, of suppressing the solubility of the catalyst support in the aqueous acid solution and/or the neutral aqueous solution, thereby to form a modified catalyst support which is less soluble or more inert in the aqueous acid solution and/or the neutral aqueous solution, than the untreated catalyst support. The modifying component may comprise foreign atoms such as Cu, Zn, Mn, Ba, Si, Co, Ni, Zr, Ce, or Mg.

The Applicant has surprisingly found that by selecting a catalyst support material with sufficient strength and an appropriate size distribution, the optimized catalyst particle size distribution of a 30 g Co/100 g $Al_2O_3$ catalyst prepared on a pre-shaped $Al_2O_3$ support with a BET surface area of 150 $m^2$/g and a BET porosity of 0.50 ml/g, according to the proprietary method, is 45 to 250 microns, and preferably 70 to 200 microns. Provided the bulk, ie at least 90% of the particles, are within the preferred size range of 70 to 200 microns after losing the portion of material smaller than the controlling dimension of the filter, the desired synthesis performance will essentially be attained. A further advantage obtained with the selection of a catalyst support material with sufficient strength and an appropriate size distribution is that the formation of fines during Fischer-Tropsch synthesis in the slurry phase reactor is largely prevented, thereby normally ensuring a liquid product that has a catalyst content less than 10 ppm (by mass).

To ensure effective reaction and optimum production rates, interaction between the said particles and gas molecules is essential, and therefore catalyst suspension is important. It has hitherto been believed that it is imperative to have a substantial proportion of relatively small catalyst particles present in the slurry bed. Particularly, in the absence of downcomers, with which the solid particulate catalyst phase can be kept in near uniform suspension by using gas bubbles, a substantial proportion of catalyst particles of the order of 30 microns have hitherto been believed to be essential.

To inhibit catalyst settling, the process may thus include agitating the slurry in the slurry bed. The agitation may include allowing slurry in the slurry bed to pass downwardly from a high level to a lower level, through at least one downcomer. Preferably, the slurry may be allowed to pass downwardly through at least one downcomer located in a first downcomer region of the slurry bed, as well as through at least one further downcomer located in a second downcomer region of the slurry bed, with the second downcomer region being spaced vertically with respect to the first downcomer region, so as to redistribute the catalyst particles within the slurry bed, as taught in ZA 98/5992 // PCT/GB98/02070 which is hence incorporated herein by reference. Thus, the downcomer(s) serve(s) to impart a nett upward liquid velocity to the slurry bed in the regions of the slurry bed outside the downcomers thereby maintaining the catalyst in near uniform suspension.

The process thus involves initially selecting a catalyst particle size distribution in a specific size range so that 18 vol %, preferably 4 vol %, more preferably 2 vol %, of the particle sizes are less than the controlling dimension of the filtering medium, thereby avoiding, or at least reducing, permanent or irreversible blinding of the filtering medium, and catalyst loss into the liquid product. The maximum particle size, which in turn determines the range of particle sizes, is then determined to avoid lower activity or poor selectivity due to intra-particle mass transfer effects. This is achieved by following known procedures, eg as illustrated in Example 4. It is preferable that more than 90% of the catalyst particles are less than the maximum particle size. Additionally, there is little or no loss of catalyst contact with the gaseous reactants due to catalyst particle settling.

The process may include operating the column such that the slurry bed is in a heterogeneous or churn-turbulent flow regime and comprises a dilute phase consisting of fast-rising large bubbles of gaseous reactants, and possibly gaseous products which traverse the reaction zone or slurry bed virtually in a plug flow manner and a dense phase comprising liquid phase, ie liquid product, solid catalyst particles and entrained smaller bubbles of gaseous reactants and gaseous product.

By passing or recirculating some of the slurry through the downcomers, more uniform redistribution of the catalyst in the slurry bed is achieved, than is the case without such downcomers. The catalyst particles in the slurry bed are thus maintained in suspension by the turbulence created by the synthesis gas stream passing through the slurry bed combined with an upward liquid velocity induced by the presence of the downcomers. It was found that the use of downcomers to keep the catalyst particles in uniform suspension, avoids the problem of catalyst settling when selecting the optimum catalyst particle size distribution. Computational fluid dynamic (CFD) modelling may be used to optimize the layout of the downcomers.

The process may thus include allowing a cake of catalyst particles to form on the filtration medium; from time to time interrupting the passage of liquid product through the filtering medium; and backflushing the filtering medium in the opposite direction to the direction of flow through the filtering medium during the separation of the liquid product from the catalyst particles, thereby to dislodge the cake from the filtering medium. The backflushing may be effected for at least portions of the periods that the liquid product passage through the filtering medium is interrupted.

A plurality of the filter elements, located at the same or different levels within the filtration zone, may be provided. The filtration zone may be provided anywhere below the upper surface of the slurry bed. The filter elements may be arranged in a plurality of banks, with each filter bank comprising a number of the-filter elements.

In principle, the elements can be located at any desired inclination; however, they are preferably located vertically with their liquid product or filtrate outlets directed downwardly.

The passage of the liquid product through the filtering media may be effected by applying a pressure differential across the filtering media and any cake build-up thereon. Preferably this pressure differential may be up to 8 bar, and is typically in the region of between 1 and 4 bar. The pressure differential may be effected by withdrawing the liquid product into a rundown vessel which is at a lower pressure than the reactor vessel, with the filtrate outlets of the filter elements being connected to the rundown vessel by means of suitable liquid product conduits. The conduits may include a primary liquid product conduit leading from the filtrate outlet of each filter element; a secondary liquid product conduit into which the primary conduits of all the filter elements of the particular bank of filter elements tie; and a tertiary liquid product conduit leading to the rundown vessel, with the secondary conduits all tying into the tertiary conduit.

The flushing fluid may be process or non-process derived liquid and/or gas, eg some of the liquid and/or gaseous product.

The backflushing may, in general, be effected in pulse-like fashion. Thus, the backflushing may comprise an initial pulse of flushing liquid and/or gas, optimally followed by one or more further pulses of flushing liquid and/or gas. Each backflushing pulse may comprise initiating backflushing rapidly, ie commencing flow of flushing fluid rapidly; and backflushing the elements rapidly with a volume of the flushing fluid. This volume of flushing fluid may be relatively large, eg approximately equivalent to the internal volume of the filter elements. It can, however, be less than the internal volume of the filter elements, eg less than half their internal volume. When the volume of flushing fluid used during the initial pulse is relatively large, the volume of flushing fluid used during a second pulse may be less than that of the initial pulse, eg less than half the internal volume of the elements. However, when the volume of flushing fluid used during an initial pulse is relatively small as hereinbefore described, then the volume of flushing fluid during a further or second pulse may be similar to that of the initial pulse. The nature of any further pulses, when utilized, and the volume of the flushing fluid used during such pulses, may be similar to those of the second pulse hereinbefore described.

The pressure differential across the filtering media and filter cake during backflushing may be up to 10 bar depending on the degree of clogging or age of the filtering media, and is typically at least 1 bar higher than the filtration pressure differential.

The flushing fluid flow rate may be at least 6000 $l/h/m^2$ of filtering media. Thus, the flushing fluid flow rate may be between 6000 $l/h/m^2$ of filtering media when the pressure differential across the filtering media is about 5 bar, and between about 10000 and 12000 $l/h/m^2$ when the pressure differential is about 10 bar.

The process may preferably include subjecting the filtering elements to a waiting period during which no filtering or backflushing takes place, ie during which there is no liquid flow through the filtering media of the elements, to enhance subsequent filtration. The waiting period may be up to 60 minutes, or even longer, but is typically less than 30 minutes.

The backflushing may thus be effected in a manner, and using backflushing means, as described in ZA 94/0582 // U.S. Pat. No. 5,599,849/U.S. Pat. No. 5,844,006, which is hence incorporated herein by reference. Thus, backflushing may be effected by propelling or forcing residual liquid product in the conduits back through the filter elements in the second direction, preferably also through a restriction orifice located in the primary conduit of each filter element, by means of pressurized gas. It has been found that cleaning of the filter element surfaces is considerably improved, thus enhancing subsequent filtering performance thereof, when backflushing with the gas is effected for at least a sufficiently long period of time to displace substantially all the residual liquid product through the restriction orifices back into the filter elements. Backflushing with gas also has the advantage that the gas thereby introduced into the reactor vessel and which is removed with the product gas, does not have to be filtered again, thereby reducing loading on the filter elements during filtration.

According to a second aspect of the invention, there is provided a process for producing liquid and, optionally, gaseous products from gaseous reactants, which process comprises feeding, at a low level, gaseous reactants into a slurry bed of solid catalyst particles suspended in a suspension liquid;

allowing the gaseous reactants to react as they pass upwardly through the slurry bed, thereby to form liquid and, optionally, gaseous products, with the reaction being catalyzed by the catalyst particles; and separating liquid product from the catalyst particles by passing, in a filtration zone within the slurry bed, liquid product through a filtering medium having a plurality of openings through which the liquid passes, with the openings having a minimum dimension of x microns, and with the proportion of catalyst particles, whose minimum dimension is less than x microns, in the slurry bed being less than 4% by volume based on the total volume of the catalyst in the slurry bed.

The invention will now be described by way of example with reference to the accompanying diagrammatic drawings.

DETAILED DESCRIPTION

Figure 1:
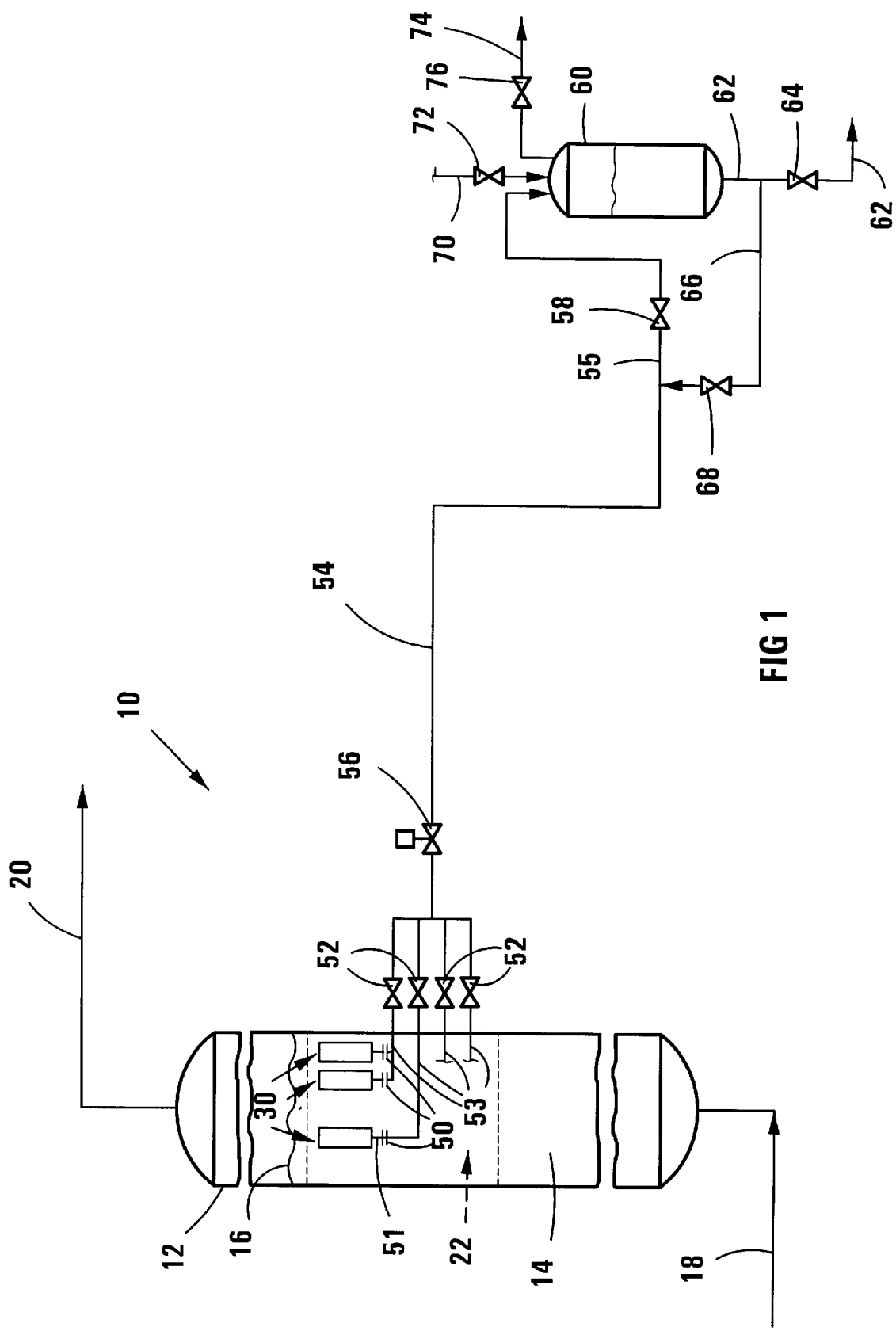
FIG. 1 shows a simplified flow diagram of a large pilot plant installation according to one embodiment of the invention, for producing gaseous and liquid products from gaseous reactants, with the downcomers omitted from the reactor vessel for clarity.
Figure 2:
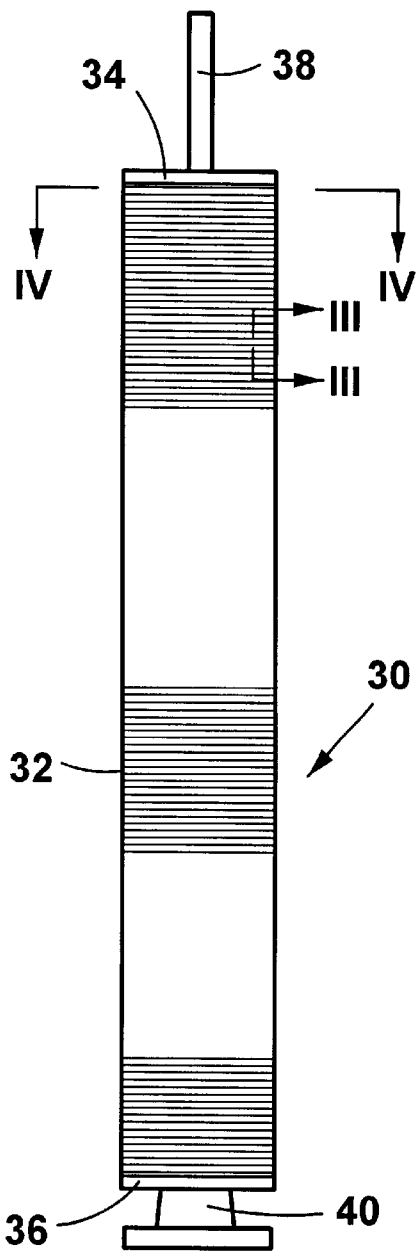
FIG. 2 shows an enlarged side view of one of the filter elements shown in FIG. 1.
Figure 3:
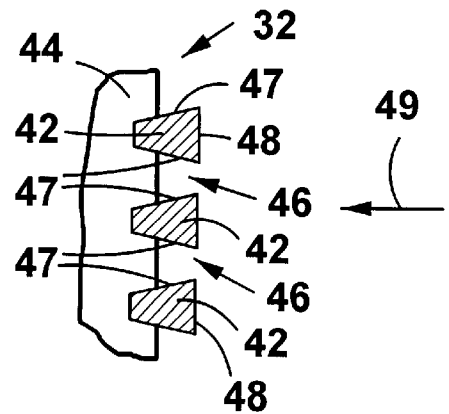
FIG. 3 shows, in part, an enlarged sectional view through III—III in FIG. 2.
Figure 4:
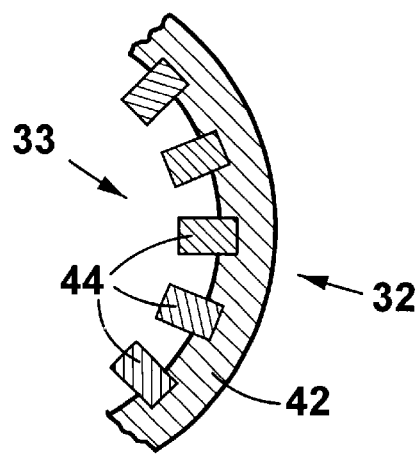
FIG. 4 shows, in part, a sectional view through IV—IV in FIG. 2.
Figure 5:
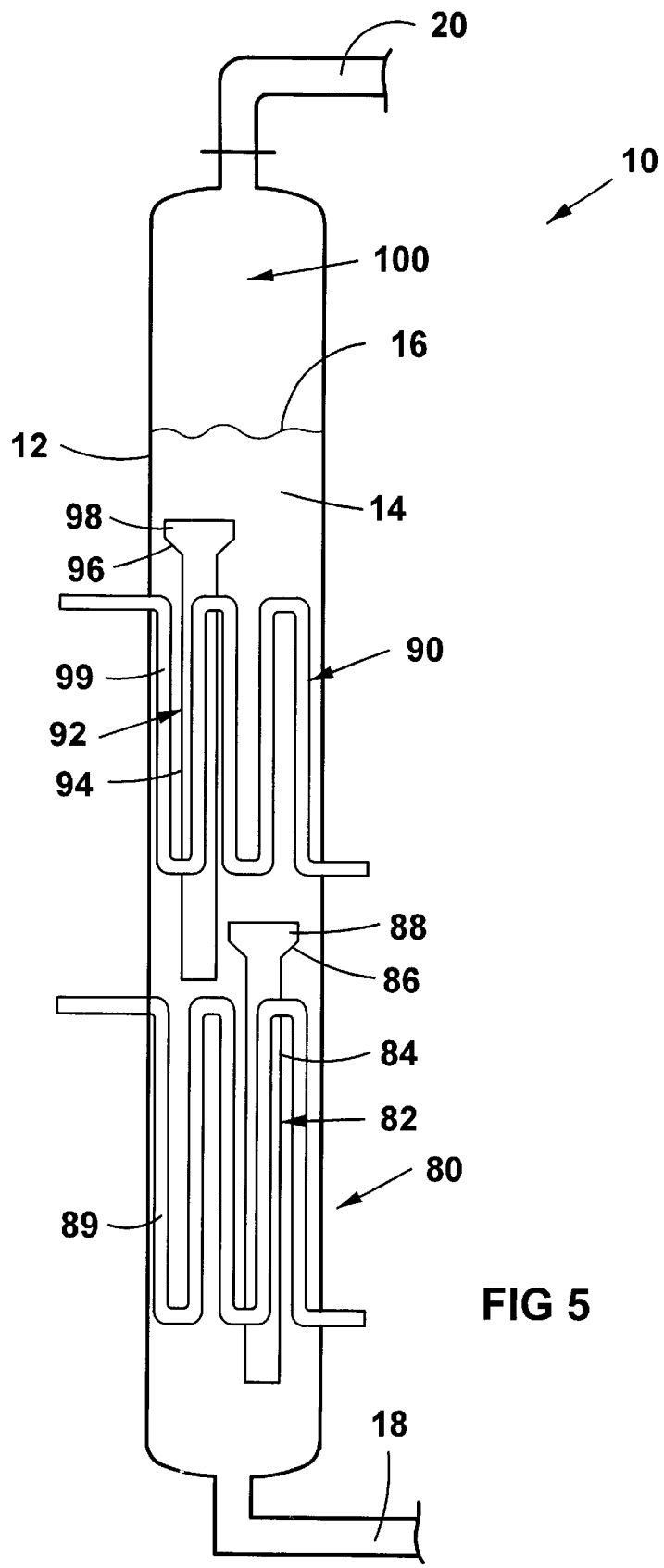
FIG. 5 shows a longitudinal sectional view of the reactor vessel of FIG. 1, with the internal filters omitted and the downcomers present.

In FIGS. 1 to 5, reference numeral 10 generally indicates an installation for carrying out a process according to the invention, for producing gaseous and liquid products from gaseous reactants.

The installation 10 includes an upright cylindrical Fischer-Tropsch synthesis slurry phase reactor vessel 12.

The vessel 12 provides a slurry bed zone normally containing a slurry bed 14 of catalyst particles suspended in liquid product and through which gas is passing, as described in more detail hereunder. The slurry bed 14 has an upper surface 16, and the expanded height of the slurry bed 14 while gas passes through it is typically between 14 and 18 m when the total reactor length is about 24 m.

A synthesis gas flow line or conduit 18 is connected to a gas inlet (not shown) provided at the bottom of the vessel 12, while a gas withdrawal flow line or conduit 20 leads from a gas outlet (not shown) provided at the top of the vessel 12. A suitable gas distributor (not shown) is connected to the gas inlet.

The installation 10 also includes a plurality of filter elements 30 (only some of which are shown) located in a filtration zone 22 within the slurry bed 14, arranged in a plurality of banks. Each filter element 30 is of elongate cylindrical form, and comprises a cylindrical filtering medium 32 enclosing a filtrate or liquid collecting zone 33. The medium 32 is located between end plates 34, 36. a mounting rod 38 protrudes from the end plate 34, while a flanged liquid outlet 40 is provided on the end plate 36.

Thus, by means of the outlet 40, filtrate or liquid can be withdrawn from the collecting zone of the element or cartridge 30. The elements 30 are mounted in position in the vessel 12 by means of the rod 38 and flanged outlets 40. This mounting is not shown in detail in the drawings, but is typically effected by connecting the rod 38 to a lattice or grid spanning the vessel 12, while the outlet is connected to a conduit as hereinafter described.

The filtering medium 32 comprises a spiral wound wire 42 embedded in, or attached to, circumferentially spaced elongate supports 44 extending between the end plates 34, 36. Filtration openings or slots 46 are thus provided between adjacent loops of the wire 42. The wire 42 has, adjacent the openings or slots 46, surfaces 47 which taper away from each other, in the direction of the collecting zone. The wire 42 thus also has surfaces 48 against which a cake of catalyst particles (not shown) will form, as described in more detail hereunder, when liquid product is filtered by the elements 30 as it passes through the slots 46 in the direction of arrow 49. As a result of the tapering surfaces 47, solid particles will not readily permanently clog or impregnate the openings or slots 46 when filtered product passes through in the direction of arrow 49.

Typically, the filter elements 30 have an external diameter of 2 to 12 cm, with the wire 42 being of stainless steel. The width of the wire 42 at its base is typically about 1.2 mm, but preferably is 0.8 mm or 0.5 mm. This ensures a lower variation in the width of the slots and reduces the number of openings in excess of the average slot width. The average width of the slots or openings 46 are typically from 10 to 25 microns, but preferably are not greater than 20 microns. This reduces the possibility of the controlling dimension of a filter being greater than desired. A catalyst content of 10 ppm or less in the filtered wax can thereby be achieved. The greater the variation in the gap size and the greater the maximum opening of any filter gap, the greater the possibility of particles larger than the average gap size passing through the filter media. Those versed in the art of filtration know that this will reduce the separation efficiency of the filtration system. It was found that this variation also increased the potential for blinding of the filters during backflushing due to the particularly hard nature of the proprietary cobalt Fischer-Tropsch catalyst. The near gap size hard catalyst particles become irreversibly lodged in the backflush side of the filter media.

Instead of the filter elements 30, any other suitable elongate filter elements or cartridges, such as ceramic or sintered metal filter elements, can be used.

The filtration zone 22 is preferably located at a high enough level within the slurry bed, so that the filter elements 30 are located outside the zone of settled catalyst if the gas supply 18 is interrupted. As a result, they will not be embedded in settled solids or catalyst on slumping of the bed 14. However, it has been found that the filtration zone 22 need not necessarily be located near the top of the slurry bed 14 but can instead be located lower down since, should such bed slump occur, it has been found permanent clogging of the filter elements 30 will still not readily occur even if the elements are completely surrounded by settled solids or catalyst. The filter elements 30 are preferably located at a low enough elevation so that they remain submerged in liquid and are not exposed to gas if the gas supply is interrupted, but filter exposure is acceptable if the filter surface is shaped so as to avoid catalyst laydown.

The elements 30 are preferably located with their outlets 40 directed downwardly so that any solid or catalyst fines which pass through the slots 46 with the filtrate (liquid product) will tend to collect in the bottom of the collection zones of the filter elements 30 from where they will be washed out with the liquid product.

To the outlet 40 of each of the filter elements 30 is connected a primary conduit 51, fitted with a restriction orifice 50. The conduits 51 of all the filter elements 30 making up a bank of the elements tie into a common secondary conduit 53 fitted with a shut-off valve 52. All the conduits 53 tie into a common tertiary conduit 54, fitted with a quick opening valve 56. A conduit 55 leads from the conduit 54 and is fitted with a shut-off or isolation valve 58. The conduit 55 leads into the top of a liquid blowdown vessel 60. A liquid rundown conduit 62, fitted with a shut-off valve 64, leads from the bottom of the vessel 60. The conduit 55 also serves as a backflushing conduit for gas. Alternatively, a liquid backflush conduit 66, fitted with a shut-off valve 68, can lead from the conduit 62, upstream of the valve 64, back to the conduit 54, between the valves 56, 58.

A pressurizing gas conduit or line 70, fitted with a control valve 72 leads into the top of the vessel 60, while a vent conduit or line 74, fitted with a control valve 76, leads from the top of the vessel 60.

The vessel or column 12 includes a first downcomer region, generally indicated by reference numeral 80. The downcomer region 80 includes a downcomer, generally indicated by reference numeral 82. The downcomer 82 includes a cylindrical transport section 84 of relatively small diameter, an outwardly flaring connecting component 86 at the upper end of the transport section 84, and a larger diameter degassing section 88, the lower end of which is connected to the connecting component 86. The upper end of the degassing section 88 thus provides an inlet for slurry, while the lower end of the transport section 84 provides a slurry outlet. A cooling coil 89 is also provided in the downcomer region 80.

The vessel or column 12 also includes a second downcomer region, generally indicated by reference numeral 90. The downcomer region 90 includes a downcomer, generally indicated by reference numeral 92. The downcomer 92 also includes a transport section 94 of relatively small diameter, an outwardly flaring connecting component 96 at the upper end of the transport section 94, and a degassing section 98 of relatively large diameter at the upper end of the transport section 94. The lower end of the degassing section 98 is thus connected to the connecting component 96. The upper end of the degassing section 98 provides a slurry inlet, while the lower end of the transport section 94 provides a slurry outlet. A cooling coil 99 is also provided in the downcomer region 90.

The lower end of the downcomer 92 is spaced with vertical clearance from the upper end of the downcomer 82. Furthermore, the downcomer 92 is not aligned axially with the downcomer 82. In other words, the downcomer 92 is staggered relative to the downcomer 82 when the vessel or column 12 is seen in plan view.

In use, synthesis gas, comprising mainly carbon monoxide and hydrogen, enters the reactor vessel 12 along the flow line 18. The gas flow rate to the vessel 12 is such as to give a superficial gas velocity in the filtration zone 22, based on the open cross-sectional area of the filtration zone, of between 5 and 70 cm/s, typically about 30 to 40 cm/s.

The slurry bed 14 is maintained in the reactor vessel 12. The slurry bed 14 comprises catalyst particles suspended in liquid product, ie liquid wax produced in the vessel 12 on reaction of the gaseous reactants. The catalyst particles are maintained in suspended state in the slurry bed 14, and in particular in the filtration zone 22, by means of the turbulence created therein by the gas passing upwardly therethrough. This turbulence also inhibits excessive cake build-up on the filtering media, and thus enhances filtration through the media.

The vessel 12 is typically maintained at an operating pressure of about 20 bar, and at an operating temperature between 180° C. and 260° C., typically about 230° C. However, the operating pressure can be in excess of 20 bar, and the operating temperature higher or lower than 230° C., as hereinbefore described, depending on the nature and spread of gaseous and liquid products required and the type of catalyst used. Naturally, the vessel 12 will be provided with suitable temperature control means, such as the cooling coils 89, 99 for controlling the reaction temperatures, as well as suitable pressure control means such as a pressure control valve.

In the vessel 12, as the synthesis gas passes through the slurry bed 14, the carbon monoxide and hydrogen react to form a range of products in accordance with known Fischer-Tropsch reactions. Some of these products are in gaseous form at the operating conditions of the vessel 12 and are withdrawn, together with unreacted synthesis gas, along the flow line 20. Some of the products produced, such as the waxes already mentioned, are in liquid form at the operating conditions of the vessel 12, and act as the suspension medium for the catalyst particles. As liquid product is formed, the level 16 of the slurry bed naturally rises, and the liquid product is thus withdrawn in the filtration zone by means of the filter elements 30 and rundown vessel 60 to maintain the slurry bed level. This internal filtration constitutes a first stage of the operating cycle of the filter elements 30.

The liquid product which passes through the filter elements 30 and which contains a relatively small concentration of solids (catalyst), if any, passes, by means of the conduits 53, 54 and 55 into the vessel 60. The vessel 60 is maintained, by means of pressurizing gas introduced along the line 70, at elevated pressure, which is, however, lower than that in the vessel 12. Typically, the pressure in the vessel 60 is set such that the pressure differential across the filtering media of the elements 30 and any filter cake build-up thereon, is about 2 to 4 bar.

In this fashion, a relatively constant slurry bed level in the reactor is maintained. However, when the filter cake has built up to some thickness, it must then be backflushed from the filtering media, in a second stage of the operating cycle of the filter elements 30. The backflushing is effected by shutting the quick opening valve 56 and valve 58, and withdrawing at least some of the liquid product in the rundown vessel 60, through the flow line 62, in order to remove any solids which have settled out in the bottom of the vessel 60. The pressure in the vessel 60 is then increased, by means of the gas pressurizing line 70, to a pressure greater than the operating pressure in the vessel 12. As a result of the static head of liquid (wax) in the rundown conduits, the liquid pressure at the quick opening valve 56 is typically slightly lower than the pressure in the vessel 60, but still sufficient for backflushing. When it is desired to backflush with liquid, the vessel 60 will thus contain some liquid product; however, if it is desired to backflush with gas, the vessel 60 will be pressurized with gas only, which can then be gaseous product such as tail gas.

Backflushing is effected in pulse-like fashion on one bank of filter elements 30 at a time, using either liquid product or gas. Thus, during backflushing, one of the valves 52 will be open, with the remaining valves 52 closed. For backflushing with liquid, valve 68 will be open, while for backflushing with gas, valve 58 will be open. In a first backflushing step, the quick opening valve 56 is opened rapidly in less than 0.8 seconds, and a volume of liquid product or gas, approximately equivalent to the internal volume of the filter elements 30 making up the bank of elements being flushed, is allowed to pass from the vessel 60, to produce a flow through the backflushing conduit 66 or 55, and the conduits 54, 53 and 51, thereby to provide flushing fluid through the bank of elements 30, in a second direction opposite to the direction in which the product flows during filtering. This typically takes up to 30 seconds. Thereafter, the quick opening valve 56 is again shut.

If a second backflushing step is desired, the vessel 60 is then again repressurized. In a second pulse-like backflushing step, the quick opening valve 56 is again opened rapidly for a second time. This time a flushing fluid volume equivalent to about one-third of the volume in the first backflushing operation, is allowed to pass from the vessel 60 to the filter elements 30. The valve 56 is thereafter again closed. If desired, at least one further similar backflushing step can be effected on that particular bank of filter elements.

The remaining barks of elements can then similarly be backflushed, by opening and closing the appropriate valves 52.

Thereafter, in a third stage of the operating cycle of each bank of filter elements 30, they are subjected to a waiting period in which no liquid passes through them. The Applicant has found that the filtration rate, when the filter elements 30 are then thereafter again subjected to filtration as hereinbefore described, increases with an increase in the duration of the waiting or non-active period. However, this must be balanced against the disadvantage that the filter elements are out of service during these waiting times. It has been found that a waiting period of between 1 and 30 minutes gives good results. It is believed that, during this waiting period, catalyst cake which has been loosened from the filter media of the elements 30 and partially broken up during the backflushing stage, is effectively broken up further, removed from the filter media surfaces and re-mixed remotely from the filters 30, by means of the turbulence within the slurry bed 14. It is believed further that the gas superficial velocity through the filtration zone 22 may influence the optimum duration of the waiting period.

Some slurry continuously passes downwardly through the downcomers 92, 82, thereby to achieve uniform redistribution of catalyst particles within the slurry bed 14, and also to ensure uniform heat distribution throughout the slurry bed, as also described in more detail hereunder.

The vessel or column 12 is operated so that the slurry bed 14 thereof is in a heterogeneous or churn-turbulent flow regime and comprises a dilute phase consisting of fast-rising larger bubbles of gaseous reactants and gaseous product which traverse the slurry bed virtually in plug flow fashion, and a dense phase which comprises liquid product, solid catalyst particles and entrained smaller bubbles of gaseous reactants and gaseous product.

Figure 6:
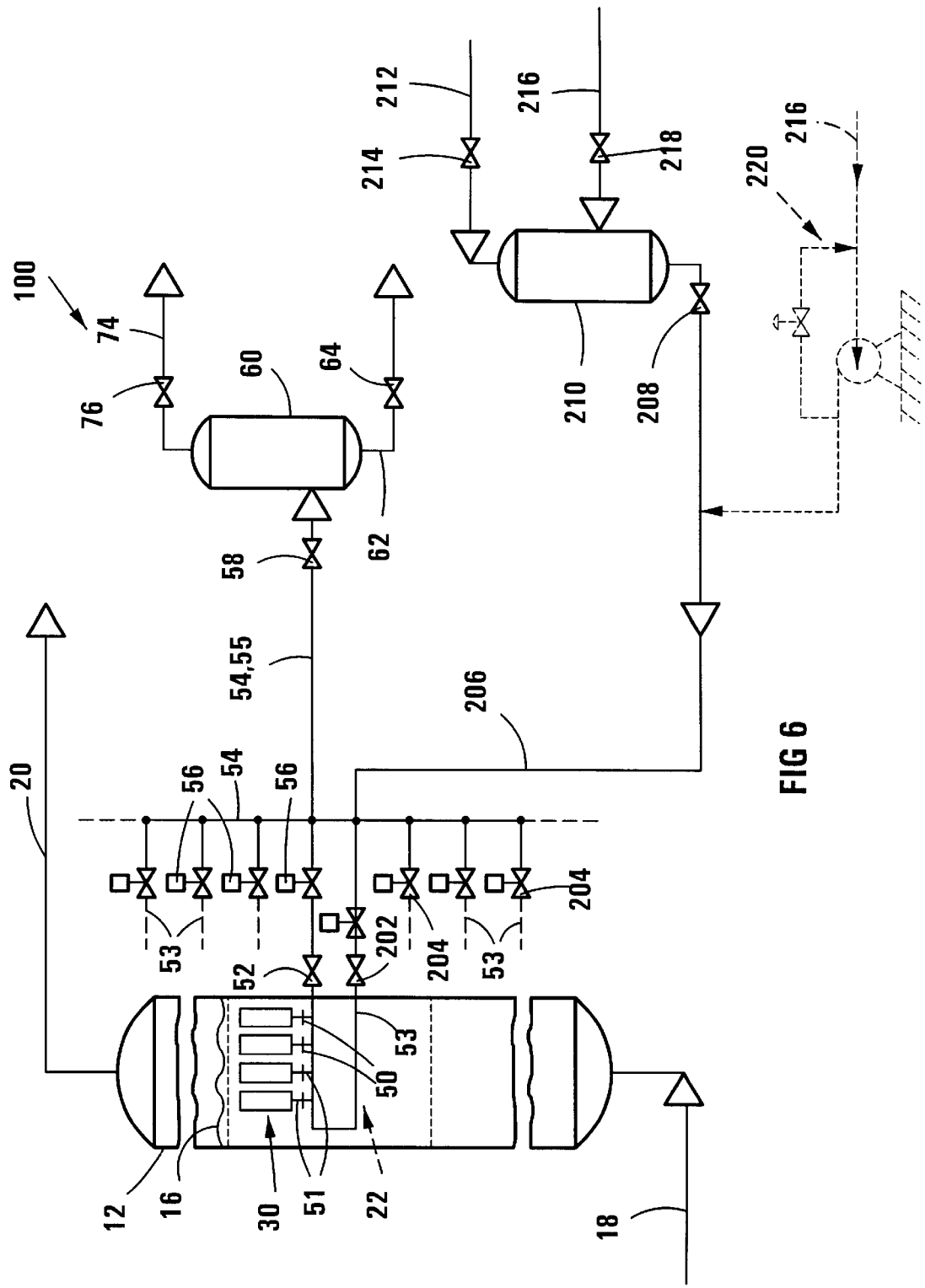
FIG. 6 shows a simplified flow diagram of an installation according to another embodiment of the invention, for producing gaseous and liquid products from gaseous reactants.

Referring to FIG. 6, reference numeral 200 generally indicates an installation according to another embodiment of the invention, for producing gaseous and liquid products from gaseous reactants.

Parts of the installation 200 which are the same or similar to those of the installation 10 hereinbefore described with reference to FIGS. 1 to 5, are indicated with the same reference numerals.

In the installation 200, each conduit 53 is provided with one of the quick opening valves 56, while the pressurizing conduit 70 for the vessel 60, and the backflush conduit 66 used in the installation 10 are dispensed with. Instead, each of the conduits 53 is in the form of a loop, with the valve 56 provided near one end of the loops, and valves 202, 204, which are similar to the valves 52, 56 respectively, near another end of the loop. The conduits 53 also tie into a common backflush fluid conduit 206, which leads from a backflush fluid vessel 210, and is fitted with a valve 208. A gas pressurizing line 212, fitted with a valve 214, leads into the vessel 210, as does a backflush liquid feed line 216, fitted with a valve 218.

For liquid backflush, the vessel 210 is supplied, by means of the flow line 216, with backflush liquid which can be, but is not limited to, filtered wax from the vessel 60. The pressure in the vessel 210 is maintained at a pressure which is preferably at least 5 bar higher than the pressure in the reactor vessel 12 by means of gas introduced along the flow line 212. The rate at which gas is introduced is preferably sufficient to prevent a drop in pressure in the vessel 210 of more than 1 bar during backflushing.

For gas backflush, no liquid is supplied to the vessel 210 which is thus filled only with gas, eg tail gas, introduced along the flow line 212.

Backflushing is effected on one bank of filter elements 30 while maintaining filtration through the remaining banks, by closing the filtration valve 56 of that bank. This is followed by rapid opening, preferably in less than 1 second, of the backflush valve 204 of that bank of elements. The backflush valve 204 remains open for a period which is sufficient for the required volume of backflush fluid to flow out of the backflush vessel 210 along the conduit 206, and is thereafter closed. Once the pressure in the backflush vessel has been restored by means of gas, the backflushing can be repeated on the same filter bank, or on the next bank of element by opening and closing the required filtering valves 56, and opening the appropriate backflush valve 204.

If desired, instead of using the backflush vessel 210, a pump 220, fitted with a controlled kickback loop, for liquid backflush, or a compressor (not shown) for gas backflush, can be used, as indicated in broken line in FIG. 6. During filtration on the installation 10, catalyst particles that pass through the filter by nature of having a nominal diameter smaller than the filter gap size can tend to settle out in the conduit 54. During backflush of the filter elements, these catalyst particles that have settled in the conduit 54 during filtration are introduced to the reverse or backflush side of the filter media. This occurs due to the higher wax flows during backflushing. The catalyst particles, if in the near gap size particle size range, can irreversibly blind the filter elements. This mechanism of blinding the filters during backflushing can be reduced, although not entirely eliminated, using different dedicated filtration and backflush vessels. These are shown as vessels 60 and 210, respectively, in the installation 200. However, in the installation 200, catalyst particles passing through a filter element into conduit 53, can still cause blinding of a filter element further downstream in conduit 53 during the backflush cycle.

Certain aspects of the process of the invention were tested, and are described in non-limiting Examples 1, 2, 3, 4 and 5 hereunder In Examples 1, 2, 3, 4 and 5, the proprietary cobalt Fischer-Tropsch catalyst used was in accordance with Example 1 of ZA 99/1265 // PCT/GB 99/00527.

EXAMPLE 1
Strong Catalyst and Particle Size Distribution

Table 1 provides a summarized comparison of the important characteristics of the applicant's proprietary cobalt Fischer Tropsch catalyst versus a particular fresh commercially available pre-shaped gamma alumina support material such as Puralox SCCa 5/150 (trademark) as supplied by Condea Chemie GmbH of Überseering 40, 22297 Hamburg, Germany.

TABLE 1

Summarized comparison of some important characteristics of catalyst support material

|  | Puralox SCCa 5/150* | Proprietary cobalt Fischer-Tropsch catalyst |
|---|---|---|
| B.E.T. surface area | 157 m²/g | 115 m²/g |
| B.E.T. pore volume | 0.47 ml/g | 0.27 ml/g |
| Average pore diameter | 120Å | 94Å |
| Structural density |  | 3.7 g/ml |
| Cobalt metal surface area |  | 13.7 m²/g freshly reduced catalyst |

*5/150) implies:
i) ca 5 vol % particles smaller than a particle size of 45 micron, also displaying a maximum particle size of ca 150 micron.
ii) a BET derived surface area of ca 150 m²/g A direct application of Example 4 describe hereinafter, resulted in an optimized particle size distribution of the applicant's proprietary cobalt Fischer-Tropsch catalyst estimated as having a particle size range distribution between 70 to 200 micron.

A sample of said Puralox SCCa 5/150 (trademark) alumina support was additionally classified to produce a product containing less than 2 vol % particles smaller than 40 micron and this resulted in significantly less than 18 vol % particles smaller than 55 micron and was loaded into a pilot plant slurry phase reactor, containing wedge wire filter elements, as hereinbefore described, with a nominal gap size of 25 microns and a controlling dimension of 55 microns.

The said Puralox SCCa 5/150 (trademark) alumina support was run in the slurry bed reactor for approximately two weeks. During this period the differential pressure (DP) across the filter was always below 1 bar and most of the time below 0.5 bar. The filtration rate during the operation was always in excess of 2000 l/m² h.

It can be concluded that the classified Puralox SCCa 5/150 (trademark) support gives excellent filtration in the slurry bed reactor. There were no signs of blockage of the filter from either side.

EXAMPLE 2
Effect of Catalyst Fines on Filter Performance

The effect of near gap size catalyst particles, ie the catalyst particle fraction between 10 and 30 μm for a wedge wire filter element with a nominal gap size of 25 μm, ie having a controlling dimension of 55 μm (derived from 25 μm+30 μm) on the filterability of higher hydrocarbon products produced by Fischer-Tropsch synthesis is shown in this example. The effect of catalyst particle sizes less than the filter controlling dimension is also shown.

Procedure for Preparing and Loading the Catalyst Fines Into the Reactor

The catalyst fines were produced by milling 35 kg of the proprietary cobalt Fischer-Tropsch catalyst. The milled catalyst was classified and the particle size distribution determined, as depicted in Table 2.

Molten wax and catalyst fines were then transferred into a loading hopper, and this vessel was pressurized to 3 bar above the slurry bubble column reactor pressure. After a differential pressure had been established, the necessary valves were opened and the slurry transferred into the reactor.

The proprietary cobalt Fischer-Tropsch catalyst was loaded into the slurry bed reactor. The reactor contents were spiked firstly using a 0 to 10 μm particle size fraction, secondly using a 0 to 20 μm size fraction, and finally using a 0 to 30 μm size fraction. Table 2 shows the details of the fines fractions.

TABLE 2

| Fines fraction | Amount loaded (g) | Fraction 0–10 μm (% vol) | Fraction 10–20 μm (% vol) | Fraction 20–30 μm (% vol) | Fraction >30 μm (% vol) |
|---|---|---|---|---|---|
| 0–10 μm | 50 | 100 (2.0) | 0 | 0 | 0 |
| 0–20 μm | 140 | 67 (4.0) | 33 (2.0) | 0 | 0 |
| 0–30 μm | 180 | 28 (2.1) | 37 (2.8) | 26 (2.0) | 9 (0.7) |

The volume fractions of fines referenced to the total volume of the total catalyst inventory of 5 kg are given in brackets.

Procedure During Each Run

For each run or test, the reactor was loaded with 5 kg of catalyst of the normal size distribution with <2 vol % smaller than 40 μm and 12 vol % smaller than 55 μm, as described in Example 1. The catalyst was introduced in wax, resulting in a solids loading of 30 mass %. Baseline operation was established at a filtration rate of 2250 l/m³ .hr at a pressure drop consistently below 0.5 bar.

Figure 7:
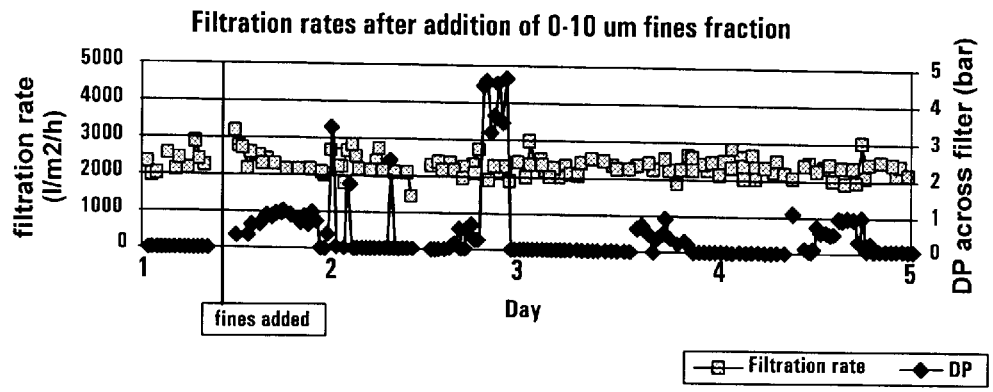
FIGS. 7 to 10 show the effect of the addition of fines on filtration performance, for Examples 1 and 2.

In a first test or run, the 0 to 10 μm fines fraction (50 g) was then added to, or spiked into, the reactor as a slurry, as hereinbefore described. Immediately after the addition of the fines the pressure drop across the filter increased to 1 bar. The filtration rate was unaffected. After a few filtration cycles the pressure drop returned to the baseline level. The filtration performance is shown in FIG. 7. A filtration cycle is defined as a liquid filtration for a period of 3 to 5 minutes, followed by a filter backflush of 3 to 5 seconds. It could then be concluded that the addition of the 2.0 vol % of 0 to 10 μm and 14 vol % <55 μm fine material had no negative influence on the filtration capacity but these particles are purged to the filtrate liquid.

Figure 8:
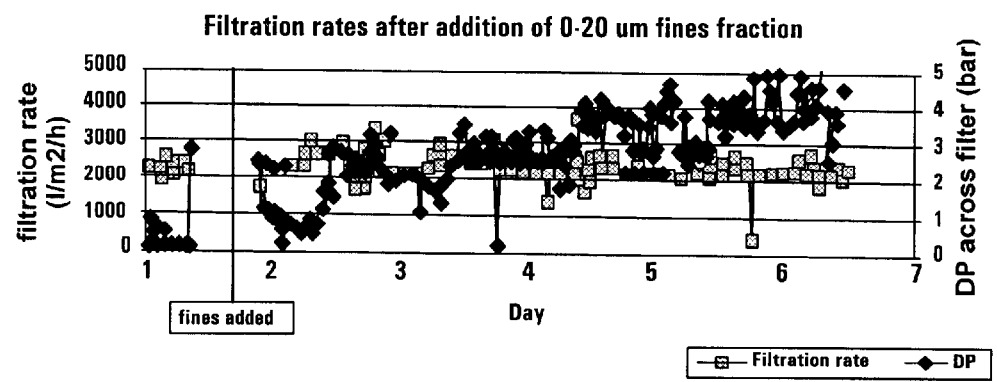

In the next test 140 kg of 0 to 20 μm fine material was slurried in wax and added to the reactor. This fraction contained 2 vol % (relative to total catalyst inventory) in the range 10 to 20 μm and 18.6 vol % <55 μm. The filter pressure drop initially increased to 2 bar after the addition of the fines but returned to below 0.5 bar shortly thereafter. A gradual increase in the filter pressure drop up to 5 bar was seen over a 4 day period. The filtration performance is shown in FIG. 8. The filtration rate was unaffected. The gradual increase in filter pressure drop was concluded to be due to a progressive binding of the filter element by the higher level of particles approaching the filter gap size. It was further concluded that the blockage occurs mainly from the reverse flow of backflushing the filter element.

Figure 9:
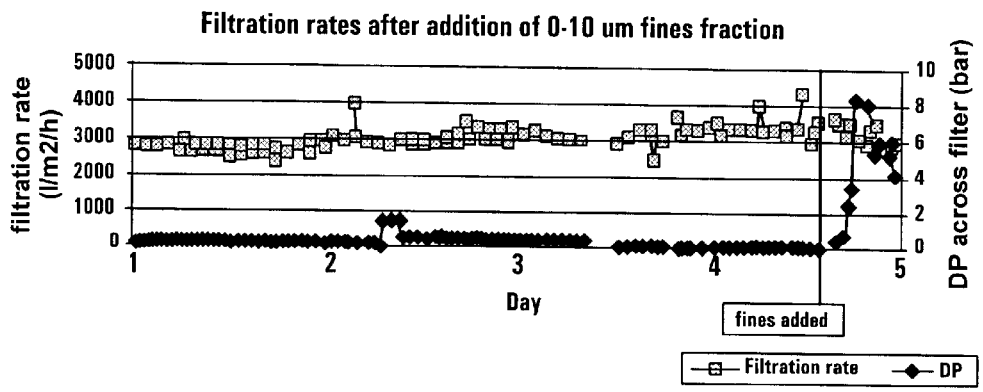

The reactor was cleaned and a new baseline established as done previously. Fine material in the size range 0 to 30 μm (180 g total, 2 vol % between 20 and 30 μm and 18 vol % <55 μm) was slurried in wax and introduced into the reactor. The filter pressure drop increased to 10 bar within a few filtration cycles. The filtration rate dropped suddenly to the extent that no further filtration was possible. The filtration performance is shown in FIG. 9. It is concluded that the fines level was such that the filter cake was too dense to allow filtration at pressure drops below or equal to 10 bar, effectively blocking the filter in the forward flow direction.

EXAMPLE 3

In a further test to demonstrate successful sustainable filtration, 5 kg of the proprietary cobalt Fischer-Tropsch catalyst of which <2 vol % were <40 $\mu$m and 12 vol % <55 $\mu$m was added to the reactor in a similar fashion to the procedure used in Example 1.

Figure 10:
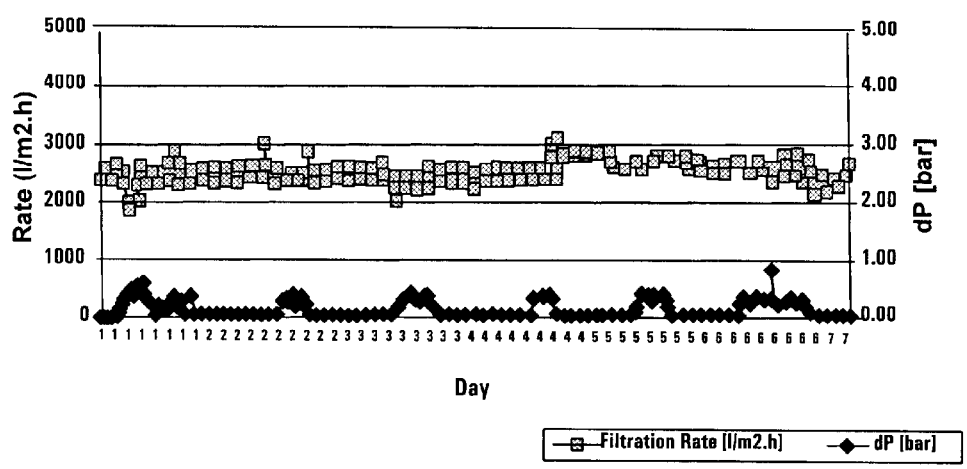

A filtration rate in the order of 2500 l/m² hr was monitored in the reactor for a period of 2 days at a filtration pressure differential of <0.5 bar. The filtration rates are shown in FIG. 10.

EXAMPLE 4

In the case of the slurry phase conversion of synthesis gas to hydrocarbons, one of the objectives is to maximize the $C_5+$ selectivities. The correlation between $C_5+$ selectivities and the structural properties of cobalt catalysts supported on $SiO_2$, $TiO_2$ and $Al_2O_3$, ie generally applicable to slurry phase cobalt based Fischer-Tropsch reactions, have been published in:

Iglesia E, Soled S. L., Fiato R. A., Journal of Catalysis, 137; 212–224 (1992) and Iglesia E., Reyes S. C., Soled S. L., Reaction-Transport Selectivity Models and the Design of Fischer-Tropsch Catalysts, ie Chapter 7 of "computer-Aided Design of Catalysts" edited by E. Robert Becker and Carmo J. Pereira, 1993, Marcel Dekker Inc, New York, Basel, Hong Kong (ISBN 0-8247-9003-0).

In these publications, a catalyst structural parameter, chi, was defined. Chi combines characteristics such as Particle size, L. expressed in m Active site density, $\theta$, expressed in terms of the number of metallic cobalt surface atoms per m² catalyst surface area Particle void fraction, $\phi$ Mean pore radius, $r_p$, expressed in m Chi was defined as the term: $[(L^2\theta\phi)r_p]$, and according to these published works, it can be postulated that the optimum (ie from a $C_5+$ selectivity point of view) range for chi is: $10^{18}m^{-1} – 10^{19}m^{-1}$.

Thus:

$$\sqrt{(r_p \times 10^{18})/(\theta\phi)} \leq L \leq \sqrt{(r_p \times 10^{19})/(\theta\phi)} \quad (1)$$

But:

$$L_{min} = \sqrt{(r_p \times 10^{18})/(\theta\phi)} \quad (2)$$

Thus: The maximum catalyst particle size $$L_{max} = \sqrt{10} L_{min}$$

$L_{min}$ with time becomes equal to the filter controlling dimension. Therefore, the filter controlling dimension may be used to determine the maximum catalyst particle size.

It has been found that parameters $\theta$, $\phi$ and $r_p$ can be selected such that $L_{min}$=79 microns, with the corresponding $L_{max}$ being 250 micron.

EXAMPLE 5

The following performance was obtained for a demonstration scale slurry phase reactor as hereinbefore described and using a particle size distribution as given hereunder, as obtained by a Malvern laser diffraction particle size analyzer. Since the particles are nominally spherical, this technique defines their diameter.

Particle size distribution:

Average particle size is 93 $\mu$m 10 vol % smaller than 62 $\mu$m 90 vol % smaller than 149 $\mu$m 1.4 vol % smaller than 46.2 $\mu$m No particles with diameters between 19 $\mu$m and 31.1 $\mu$m were detected.

a. Synthesis Performance

| | |
|---|---|
| Feed gas Flow rate | 6039 Nm³/hr |
| $H_2$ | 48.1% (v/v) |
| CO | 21.1% (v/v) |
| Reactor Open Area | 0.58 m² |
| Temperature | 230° C. |
| Pressure | 20 bar |
| Catalyst inventory | 778 kg |
| CO + $H_2$ Conversion | 66.1% | b. Filter Performance

| | |
|---|---|
| Filter type | Wedge wire |
| Wire thickness | 0.8 mm |
| Nominal Gap size | 10 micron, +30 −10 $\mu$m* |
| Diameter | 30 and 70 mm |
| Filtration rate | 2000 to 8000 l/m²/hr |

Filtration pressure drop 2 to 4 bar

The resulting catalyst concentration in the filtrate was less than 10 ppm.

The catalyst was found to be breakup resistant as defined by:

i) Catalyst concentration in the filtrate was less than 10 ppm(m)

ii) No evidence of any catalyst breakup was found by particle size distribution measurements on catalyst samples drawn from the slurry bed reactor or by scanning electron micrographs taken of catalyst particles isolated from the filtrate after 4800 hours of operation.

It has thus, in the process of the invention, surprisingly been found that, for the preferred proprietary catalyst, the preferred catalyst particle size range for optimum synthesis performance is such that all catalyst particles are larger than the apertures of commercially available filter media. This means that no compromise is necessary in terms of overlap of particle size range and filter medium aperture size range. Since there is no significant break-up of catalyst particles, this ideal situation is maintained for the full catalyst life. The catalyst life for the preferred catalyst will be several years (at least two years and possibly up to 8 years).

It has further surprisingly been found that, for the preferred proprietary catalyst and using the preferred catalyst particle size range, optimum synthesis performance is obtained, while largely avoiding the problems of catalyst loss from the reactor, blockage of the filter medium and catalyst settling, ie undesirable catalyst concentration profiles. Furthermore, this ideal situation is maintained for the entire useful catalyst life of several years.

The invention thus provides a continuous slurry phase process for Fischer Tropsch synthesis having the unique combination of a selected catalyst size distribution and means, eg downcomers, for imposing an upward liquid velocity, that avoids, or at least minimizes, practical problems such as catalyst loss, blinding of the filter media and catalyst settling.

In particular the invention provides for the design of an optimum catalyst particle size distribution of a slurry phase Fischer-Tropsch catalyst to effect maximum synthesis performance as well as trouble free extended continuous operation in a reactor system equipped with internal filter system (s) and multiple downcomers.

The invention thus solves the extremely difficult problem of optimum solid-liquid separation experienced in the art in that it provides for a selected catalyst support material with sufficient strength and an appropriate size distribution thus (a) Maintaining the catalyst particle size during Fischer-Tropsch synthesis in the slurry phase reactor;

(b) Ensuring optimum catalyst activity during Fischer-Tropsch synthesis in the slurry phase reactor;

(c) Preventing the formation of fines during Fischer-Tropsch synthesis in the slurry phase reactor to avoid irreversible blinding of filter systems in the slurry phase reactor during backflushing; and (d) Ensuring a wax product with a catalyst content lower than 10 ppm.

The invention involves keeping the catalyst particles in near uniform suspension and distribution throughout the synthesis process in the slurry reactor by making use of means, eg downcomers, for imposing an upward liquid velocity in the slurry bubble column, as hereinbefore described.

Additionally, it was also surprisingly found that the catalyst particle size distribution can be optimized having regard only to the catalyst activity and selectivity. The invention thus provides for an optimization of a three-phase slurry bubble column process provided with a multiple downcomer system, to prevent catalyst settling. The optimization resides specifically in the selection of an optimum catalyst particle size distribution that is dependent only on the filter gap size for setting the lower catalyst particle size and on the catalyst productivity and intra particle mass transfer constraints in determining the upper limit particle size.

A problem occurring necessarily in known slurry phase reactor systems involving filtration to separate a liquid product from the catalyst in the slurry, is the break-up of catalyst particles which results in catalyst fines causing decreased filter efficiency for the separation of the liquid product. Fundamental filtration studies and optimization of primary filtration, including testing of filters, highlighted the fact that for optimization of the continuous slurry phase Fischer-Tropsch reaction quality control on the catalyst and the filters is essential. The inventors have thus now surprisingly found the means to optimize a continuous Fischer Tropsch slurry phase process by providing a Fischer-Tropsch catalyst to effect maximum synthesis performance as well as avoiding catalyst break-up causing catalyst fines that will decrease the filtration rate as well as increase the amount of catalyst in the filtrate liquid.

To avoid blinding of filter systems when using strong supported catalysts, it is imperative to minimize near gap size catalyst particles, ie that fraction of catalyst particles that falls in the same size range as the gap sizes of the filter in use. Commercially available Fischer-Tropsch catalyst supports typically contain 2% to 10% near-gap-size particles. Spiking experiments, with catalysts of different particle sizes, were conducted, as hereinbefore described. The Applicant has found that the presence of said near gap-size particle fraction influenced the filtration performance in the slurry phase reactor during separation of the wax product from the catalyst. Removal of these near-gap-size fractions enhanced the filtration significantly. Efficient filtration, with no blinding of the filter system, was experienced on all of the above said filter systems if the amount of fines below the controlling dimension of the filter was minimized to less than 18 vol % when using a 114 mm diameter USF Johnson (trademark) wedge wire filter with a nominal gap size of 25 microns and a controlling dimension of 55 $\mu$m.

The catalyst concentration in the filtrate was kept below 10 ppm by using a catalyst size distribution of less than 2 vol % below 40 $\mu$m when using a 30 mm or 70 mm diameter Unislot (trademark) wedge wire filter with a nominal gap size of 10 $\mu$m and a controlling dimension of 40 $\mu$m.

The process of the invention typically forms part of the conversion of natural gas to high quality diesel, kerosene and naphtha products making use of the slurry phase distillate process.

The slurry phase distillate process comprises mainly three process steps. In the first process step natural gas is converted to synthesis gas, ie a mixture of carbon monoxide and hydrogen. In the second step the synthesis gas is converted into mainly higher hydrocarbons, typically waxy products, by means of a slurry phase reactor in the presence of a selected catalyst. Other products may include a gaseous stream consisting of light hydrocarbons and a small amount of unconverted synthesis gas; condensed hydrocarbon liquid and a reaction water stream. In the third step the condensed liquid hydrocarbon stream as well as the waxy product stream may then be further treated or upgraded to middle distillate fuels, such as kerosene, diesel and naphtha.

The process of the invention thus constitutes the second step of the slurry phase distillate process.

What is claimed is:

1. A process for producing liquid and gaseous products from gaseous reactants, which process includes selecting a strong supported solid particulate Fischer-Tropsch catalyst having fine particles smaller than x microns, with the proportion of these fine particles being less than 18% by volume of the catalyst, and all the catalyst particles being smaller than 250 microns;

feeding, at a low level, a synthesis gas stream comprising mainly carbon monoxide and hydrogen, into a slurry bed of the catalyst suspended in a suspension liquid;

allowing the carbon monoxide and hydrogen to react as they pass upwardly through the slurry bed, thereby to form, by means of a Fischer-Tropsch synthesis reaction, liquid and gaseous hydrocarbon products, with the suspension liquid being liquid product, and with the reaction being catalyzed by the Fischer-Tropsch catalyst; and separating liquid product from the catalyst particles by passing, in a filtration zone within the slurry bed, liquid product through a filtering medium having a plurality of openings through which the liquid passes, with the openings having a controlling dimension that permits only fine catalyst particles smaller than x microns that are initially present in the catalyst to pass through the filter openings, wherein x$\leq$55, and with the catalyst being sufficiently strong so that substantially no catalyst particles smaller than x microns are thereafter formed.

2. A process according to claim 1, wherein the proportion of catalyst particles smaller than x microns in the catalyst is less than 4 vol %.

3. A process according to claim 2, wherein the proportion of catalyst particles smaller than x microns in the catalyst is less than 2 vol %.

4. A process according to claim 1, wherein the catalyst particles are spherical so that the size of each particle is its diameter, and wherein x is 40 microns.

5. A process according to claim 4, wherein the filtering medium is a wedge wire filtering medium comprising parallel wires which are spaced so as to provide openings whose average widths are 10 microns, so that the filtering medium has a nominal opening or gap size of 10 microns, with the filtering medium having a maximum gap size or controlling dimension of 40 microns, with the catalyst thus initially containing less than 80% by volume of catalyst particles having a diameter less than 40 microns.

6. A process according to claim 1, wherein the slurry bed is provided in a vessel, with unreacted reactants and gaseous product being withdrawn from the vessel above the slurry bed, and the separated liquid product also being withdrawn from the vessel, and with the vessel being maintained at elevated pressure and temperature conditions associated with Fischer-Tropsch synthesis.

7. A process according to claim 1, which includes agitating the slurry in the slurry bed by allowing slurry in the slurry bed to pass downwardly from a high level to a lower level, through at least one downcomer located in a first downcomer region of the slurry bed, as well as through at least one further downcomer located in a second downcomer region of the slurry bed, with the second downcomer region being spaced vertically with respect to the first downcomer region, so as to redistribute the catalyst particles within the slurry bed.

8. A process according to claim 1, which includes allowing a cake of catalyst particles to form on the filtration medium; from time to time interrupting the passage of liquid product through the filtering medium; and backflushing the filtering medium in the opposite direction to the direction of flow through the filtering medium during the separation of the liquid product from the catalyst particles, thereby to dislodge the cake from the filtering medium, with the backflushing being effected for at least portions of the periods that the liquid product passage through the filtering medium is interrupted.

* * * * *